(12) United States Patent
Hobai et al.

(10) Patent No.: US 7,109,169 B2
(45) Date of Patent: Sep. 19, 2006

(54) METHOD FOR TREATING HEART FAILURE BY INHIBITING THE SARCOLEMMAL SODIUM/CALCIUM EXCHANGE

(76) Inventors: Ion A. Hobai, 225 Walden St. #6R, Cambridge, MA (US) 02140; Brian O'Rourke, 25 Bellclare Cir., Sparks, MD (US) 21152

( * ) Notice: Subject to any disclaimer, the term of this patent is extended or adjusted under 35 U.S.C. 154(b) by 47 days.

(21) Appl. No.: 10/610,735

(22) Filed: Jun. 30, 2003

(65) Prior Publication Data
US 2004/0009894 A1  Jan. 15, 2004

Related U.S. Application Data

(60) Provisional application No. 60/392,601, filed on Jun. 28, 2002.

(51) Int. Cl.
*A61K 38/10* (2006.01)
*A61K 38/02* (2006.01)

(52) U.S. Cl. .............................. 514/13; 514/2; 530/326
(58) Field of Classification Search .................... 514/2, 514/13; 530/300, 326
See application file for complete search history.

(56) References Cited

U.S. PATENT DOCUMENTS 6,025,193 A * 2/2000 Weiss ...................... 435/320.1
6,239,124 B1 * 5/2001 Zenke et al. ................ 514/183

FOREIGN PATENT DOCUMENTS

EP    1226830 A2 *   7/2002

OTHER PUBLICATIONS

Condrescu et al. "Mode-Specific Inhibition Of Sodium-Calcium Exchange By Cyclosporin A". Biophysical Journal. Jan. 2001, vol. 80 (1 Part 2), p. 40a.*
Deonarain. Ligand-targeted receptor-mediated vectors for gene delivery. Expert Opinion on Therapeutic Patents. 1998, vol. 8, No. 1, pp. 53-69.*
Shannon et al. Interaction of cardiac Na—Ca exchanger and exchange inhibitory peptide with membrane phospholipids. American Journal of Physiology. 1994, vol. 266 (Cell Physiol. 35), pp. C1350-C1356.*
Wakimoto et al. Targeted Disruption of Na+/Ca2+ Exchanger Gene Leads to Cardiomyocyte Apoptosis and Defects in Heartbeat. The Journal Of Biological Chemistry. Nov. 24, 2000. Vol. 275, No. 47, pp. 36991-36998.*
Bassani, R. A., J. W. Bassani, et al. (1992). "Mitochondrial and sarcolemmal Ca2+ transport .reduce [Ca2+]i during caffeine contractures in rabbit cardiac myocytes." J Physiol.453: 591-608.
Bassani, R. A., A. Mattiazzi, et al. (1995). "CaMKII is responsible for activity-dependent acceleration of relaxation in rat ventricular myocytes." Am J Physiol 268(2 Pt 2): H703-12.
Chin, T. K., K. W. Spitzer, et al. (1993). "The effect of exchanger inhibitory peptide (XIP) on sodium-calcium exchange current in guinea pig ventricular cells." Circ Res 72(3): 497-503.

Cohn, J. N. (2000). "Heart failure: future treatment approaches." Am J Hypertens 13(5 Pt 2): 74S-78S.
Dipla, K., J. A. Mattiello, et al. (1999). "The sarcoplasmic reticulum and the Na+/Ca2+ exchanger both contribute to the Ca2+ transient of failing human ventricular myocytes." Circ Res 84(4): 435-44.
Enyedi, A. and J. T. Penniston (1993). "Autoinhibitory domains of various Ca2+ transporters cross-react." J Biol Chem 268(23): 17120-5.
Fabiato, A. (1983). "Calcium-induced release of calcium from the cardiac sarcoplasmic reticulum." American Journal of Physiology 245: C1-C14.
Grynkiewicz, G., M. Peonie, et al. (1985). "A new generation of Ca2+ indicators with greatly improved fluorescence properties." Journal of Biological Chemistry 260: 3440-3450.
Gwathmey, J. K., L. Copelas, et al. (1987). "Abnormal intracellular calcium handling in myocardium from patients with end-stage heart failure." Circ Res 61(1): 70-6.
Hasenfuss, G., W. Schillinger, et al. (1999). "Relationship between Na+-Ca2+-exchanger protein levels and diastolic function of failing human myocardium." Circulation 99(5):641-8.
Hobai, I. A., J. A. Bates, et al. (1997). "Inhibition by external Cd2+ of Na/Ca exchange and L-type Ca channel in rabbit ventricular myocytes." Am J Physiol 272(5 Pt 2): H2164-72.
Hobai, I. A., J. C. Hancox, et al. (2000). "Inhibition by nickel of the L-type Ca channel in guinea pig ventricular myocytes and effect of internal cAMP." Am J Physiol Heart Circ Physiol 279(2): H692-701.
Hobai, I. A. and B. O'Rourke (2000). "Enhanced Ca2+-activated Na+-Ca2+ exchange activity in canine pacing-induced heart failure." Circ Res 87(8): 690-8.
Hobai, I. A. and B. O'Rourke (2001). "Decreased sarcoplasmic reticulum calcium content is responsible for defective excitation-contraction coupling in canine heart failure." Circulation 103(11): 1577-84.
Kassiri, Z., R. Myers, et al. (2000). "Rate-dependent changes of twitch force duration in rat cardiac trabeculae: a property of the contractile system." J Physiol 524 Pt 1: 221-31.
Li, Z., D. A. Nicoll, et al. (1991). "Identification of a peptide inhibitor of the cardiac sarcolemmal Na+- Ca2+ exchanger." J Biol Chem 266(2): 1014-20.
O'Rourke, B., D. A. Kass, et al. (1999). "Mechanisms of altered excitation-contraction coupling in caninetachycardia-induced heart failure, I: experimental studies." Circ Res 84(5): 562-70.

(Continued)

*Primary Examiner*—Jeffrey Edwin Russel
(74) *Attorney, Agent, or Firm*—Peter F. Corless; Edwards Angell Palmer & Dodge LLP

(57) ABSTRACT

The present invention discloses a method of enhancing cardiac contractility in a subject with heart failure. The method consists of administering a compound that inhibits the sarcolemmal sodium/calcium exchanger, whose activity is elevated in heart failure. This method results in correction of cellular calcium handling and enhancement of cardiac contractility to healthy levels. This method can be used for treatment of acute heart failure, cardiogenic shock and congestive heart failure.

8 Claims, 6 Drawing Sheets

OTHER PUBLICATIONS

Pogwizd, S. M. (2000). "Increased Na(+)-Ca(2+) exchanger in the failing heart." Circ Res 87(8): 641-3.

Schouten, V. J. (1990). "Interval dependence of force and twitch duration in rat heart explained by Ca2+ pump inactivationin sarcoplasmic reticulum." J Physiol 431: 427-44.

Sipido, K. R., P. G. Volders, et al. (2000). "Enhanced Ca2+ released and Na/Ca exchange activity in hypertrophied canine ventricular myocytes: potential link between contractile adaptation and arrhythmogenesis." Circulation 102(17): 2137-44.

Spinale, F. (1996). Pathophysiology of tachycardia-induced heart failure. Armonk, NY, Futura Publishing Company, Inc., 1-13.

Studer, R., H. Reinecke, et al. (1994). "Gene expression of the cardiac Na+-Ca2+ exchanger in end-stage human heartfailure." Circ Res 75(3): 443-53.

Watano, T., J. Kimura, et al. (1996). "A novel antagonist, No. 7943, of the Na+/Ca2+ exchange current in guinea-pig cardiac ventricular cells." Br J Pharmacol 119(3): 555-63.

* cited by examiner

SEQUENCE LISTING

```
<160> NUMBER OF SEQ ID NOS: 1

<210> SEQ ID NO 1
<211> LENGTH: 20
<212> TYPE: PRT
<213> ORGANISM: mammalian

<400> SEQUENCE: 1

Arg Arg Leu Leu Phe Tyr Lys Tyr Val Tyr Lys Arg Tyr Arg Ala Gly
1               5                   10                  15

Lys Gln Arg Gly
            20
```

METHOD FOR TREATING HEART FAILURE BY INHIBITING THE SARCOLEMMAL SODIUM/CALCIUM EXCHANGE

CROSS REFERENCE TO RELATED APPLICATIONS

This application claims the benefit of U.S. provisional application Ser. No. 60/392,601 filed Jun. 28, 2002, and the complete contents of that application are incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license to others on reasonable terms as provided for by the terms of Contract No. R01-HL61711 awarded by the U.S. Department of Health and Human Services National Institutes of Health National Heart Lung and Blood Institute.

FIELD OF THE INVENTION

The present invention provides compositions and methods for treating and preventing heart disease by improving cardiac contractile force.

BACKGROUND OF THE INVENTION

Congestive Heart Failure

Heart failure currently affects more than two million Americans and its economic and human toll will continue to increase as the population ages. Congestive heart failure is the most common inpatient diagnosis for patients 65 years old and older, [Funk, 1996 #14], with more than 400,000 new cases reported each year [Cohn, 1991 #15]. The prognosis is poor, with 60% mortality within 5 years [Cohn, 1991 #15], and 23–52% of deaths attributable to fatal arrhythmias (sudden cardiac death; SCD) [Investigators, 1992 #17; Cohn, 1991 #15].

Heart failure is an inability to match cardiac output to physiological demand. Heart failure is therefore not a specific disease, but a syndrome that represents the end-point of most cardiac diseases, including ischemic heart disease, cardiomyopathies (dilative, restrictive, or hypertrophic), valvular heart diseases and long term hypertension and diabetes. In addition, the symptoms of heart failure can also present acutely (i.e. acute heart failure, or cardiogenic shock) in instances as acute myocardial infarction, post cardiac surgery (stunning, hybernation) or post re-vascularization therapy (i.e. reperfusion injury, post thrombolysis, percutaneous transluminal coronary angioplasty or coronary artery by-pass grafting).

Heart Failure and Cellular Excitation-Contraction Coupling

A momentous discovery was made in the early 1990s, when it was demonstrated that heart failure is ultimately due to changes at the level of the heart cells, which are unable to develop sufficient contractile force. At a cellular level, cardiac contractile force depends on the amplitude of the transient rise in calcium during the action potential (i.e. the $Ca_i$ transients). The chain of events that link membrane depolarization during the action potential to the $Ca_i$ transient is called excitation-contraction coupling (ECC). Central to the current model of ECC in heart lies the process of Ca-induced Ca-release (CICR) [Fabiato, 1983 #26]. During the action potential, membrane depolarization opens sarcolemmal Ca channels and allows Ca entry into the cell (which can be measured as L-type Ca current, $I_{Ca,L}$). Sarcolemmal L-type Ca channels are in close apposition to the intracellular release channels of the sarcoplasmic reticulum (SR, the internal Ca stores), also known as ryanodine receptors (RyR). Entry through L-type Ca channels triggers the opening of the RyR, followed by a large efflux of Ca from the SR into the cytosol. The rise in cytosolic $Ca_i$ activates the actin-myosin interaction. The subsequent cell shortening and force development will thus depend on both the $Ca_i$ transient amplitude and the myolilament sensitivity for Ca. In turn, the amplitude of the $Ca_i$ transients will depend on the amplitude of the trigger $I_{Ca,L}$ as well as the amount of Ca stored in the SR (the SR Ca load, $Ca_{SR}$).

In diastole, heart relaxation is brought about by $Ca^{2+}$ removal from cytoplasm, mainly by two mechanisms: about 70% of $Ca^{2+}$ is taken up into the SR though the action of the SR Ca pump, and is made available for next Ca release episode. The remainder 30% of cytosolic Ca is extruded from the cell by the sarcolemmal sodium/calcium exchanger (NCX).

In failing heart cells, the ECC process is corrupted, and cytosolic $Ca^{2+}$ ($[Ca^{2+}]_i$) does not rise sufficiently during the action potential to activate the required myofilament force [Gwathmey, 1987 #109]. A typical failing heart cell shows a decrease in the ability of the internal stores (the SR) to load with $Ca^{2+}$, due to a downregulation of SERCA [O'Rourke, 1999 #46]. Another component of altered $Ca^{2+}$ handling in both human disease [Studer, 1994 #79] and animal models [Hobai, 2000 #37; Pogwizd, 1999 #42] is an increase in $Ca^{2+}$ extrusion from the cell by the NCX due to NCX overexpression. However, it has been previously unclear whether NCX overexpression is compensatory or one of the primary deficits. One widely held theory has been that NCX overexpression compensated for decreased $Ca^{2+}$ re-uptake into the SR in diastole by increasing $Ca^{2+}$ extrusion from the cell [Hasenfuss. 1999 #91], which improved relaxation (positive lusitropic), but at the cost of a further depletion of SR $Ca^{2+}$ stores (negative inotropic). Further complicating the issue was the observation that NCX overexpression has also been found in hypercontractile models with no SR dysfunction [Sipido, 2000 #36].

Approved and Experimental Treatment Strategies

Despite continuous improvements, the treatment of heart failure is at this time unsatisfactory. Although the foundation of this disease is represented by the decrease in cardiac contractility, only two classes of drugs are approved for use to increase cardiac force (i.e. positive inotropes), cardiac glycosides (like digoxin) and beta-adrenergic agonists (like dobutamine, amrinone or milrinone). Importantly, despite an effective relief of symptoms, the use of these agents has been associated with no change (digoxin) or an increase (beta-adrenergic agonists) in mortality.

Other classes of agents used in heart failure exert their beneficial effects by preventing the long term cardiac remodeling (angiotensin convertin enzyme inhibitors, like captopril, and beta adrenergic blockers, like carvedilol) or by interfering with renal and vascular contributory mechanisms (like diuretics and nitrates). The long term beneficial effect of beta blockers is evident only after an initial, transient decrease in cardiac inotropy, with negative effects on both physician confidence and patient compliance. The need for new, effective positive inotropic drugs is, therefore, hard to overemphasize.

Numerous experimental therapeutic strategies have been or are currently evaluated.

Gene therapy strategies include altering the ratio of SERCA2a and phospholamban in the heart (pending patent to Rosenzweig, Hajjar, Guerrero, Luis; entitled "Use of agents to treat heart disorders"; Ser. No.: 789894; filed Feb. 21, 2001).

DESCRIPTION OF PRIOR ART

The increase in NCX has been associated with congestive heart failure since 1989 (e.g. Nakanishi, et al, 1989, Am J Physiol, 257, 2 Pt 2, H349–56.). NCX overexpression has been generally thought of as compensatory and beneficial for cell relaxation (e.g. Studer, et al., 1994, Circ Res, 75, 3, 443–53.) and, until now, it has not been envisaged that its inhibition may be beneficial.

A recent review (Sipido, et al., "Altered Na/Ca exchange activity in cardiac hypertrophy and heart failure: a new target for therapy?" *Cardiovasc Res* 53, 782–805, 2002) discusses the complexity of NCX role in failing hearts, and concludes that "Consequently, can not simply consider block of the exchanger function as a strategy in hypertrophy or heart failure in general". The authors do not discuss any means for NCX inhibition either.

Kanebo, Ltd. of Tokyo, Japan has developed a $Na^+/Ca^{2+}$ exchange inhibitor compound KB-R7943. Despite the manufacturer's claims, KB-R7943 is completely non-specific in action and inhibits a variety of ion channels in the cardiac membrane. It has been shown that the compound inhibits predominantly the Ca-entry mode of the Na/Ca exchanger and has no effect on cardiac contractility (Satoh, et al. *Circulation* 101, 1441–6, 2000). Therefore, it appears that KB-R7943 does not represent a clinically useful drug for the treatment of heart failure, nor has it been proposed to be one.

SUMMARY OF THE INVENTION

The present invention to provides compositions and methods for improving cardiac contractile force by inhibiting the sarcolemmal sodium/calcium exchanger. This can be achieved by using either pharmacological sodium/calcium exchange inhibitors, peptides, gene transfer or gene knockdown methodologies such as RNA interference or anti-sense oligonucleotides. This method can be used for treatment of both congestive heart failure due to, for example, dilative, hypertrophic or restrictive cardiomyopathy or ischemic heart disease. This method can be used for treatment of acute heart failure such as cardiogenic shock. In the context of congestive heart failure, this method can be used for both symptomatic relief and for prevention of progression of heart disease and reduction of mortality.

Compositions and methods of treatment and prevention of heart failure are provided to enhance cardiac contractility by inhibiting the sarcolemmal sodium/calcium exchanger. In one embodiment the method is used for treating congestive heart failure. Embodiments of the method of treating congestive heart failure include those where the heart failure is caused by a cardiomyopathy, including embodiments where the cardiomyopathy is dialative, restricitve, or hypertrophic cardiomyopathy.

In another embodiment the method comprises treating or preventing an acute heart failure. A further embodiment of the method is where the acute heart failure is a carcinogenic shock.

In one embodiment of the method the treatment and prevention includes administering to a subject an effective amount of a pharmaceutical composition useful to inhibit the sarcolemmal sodium/calcium exchanger. In another embodiment the pharmaceutical composition comprises at least one peptide. The peptide can the formula RRLL-FYKYVYKRYRAGKQRG (SEQ. ID. NO 1.). Other embodiments include the method as accomplished by a gene transfer, anti-sense nucleotide techniques, or RNA interference techniques.

The present invention identifies a new class of positive inotropic drugs, the NCX inhibitors. The invention originated from a detailed analysis of the cellular mechanisms responsible for the generation of cardiac contractile force and for its degradation in heart failure, as detailed below. One causative mechanism of congestive heart failure is the decreased $Ca^{2+}$ recirculation between cytosol and the internal stores located in the SR. This is due to a reduction of the SR $Ca^{2+}$ uptake mechanism, the SR $Ca^{2+}$ pump (SERCA) and an increase in sarcolemmal $Na^+/Ca^{2+}$ exchange. In effect, $Ca^{2+}$ extrusion from the cell is enhanced relative to re-uptake into intracellular $Ca^{2+}$ stores, resulting in a decrease in the amount of $Ca^{2+}$ stored in the SR and available for release. One beneficial effect of the enhanced $Na^+/Ca^{2+}$ exchange is that it helps to prevent excessive prolongation of $Ca^{2+}$ removal from the cytoplasm that would be a consequence of the impaired SERCA function. Therefore, a major therapeutic challenge is to decrease $Na^+/Ca^{2+}$ exchange-mediated $Ca^{2+}$ extrusion from the cell without impeding cell relaxation.

A novel aspect of the invention is that NCX inhibition restores contractility in cardiac cells from failing hearts without a detrimental effect on diastolic $Ca^{2+}$ handling. The lack of a specific pharmacological inhibitor was circumvented by using a peptide (XIP) that selectively inhibits the $Na^+/Ca^{2+}$ exchange. Contrary to predictions, NCX inhibition was not associated with slowing of relaxation of heart cells. This was due to the restitution of the SR uptake ability in failing cells, secondary to the increase in average $Ca_i$ mediated by NCX block. $Ca_i$ activation of SERCA has been observed previously, but has not been recognized for its importance for heart failure therapy. By indirectly increasing SR uptake in heart failure, NCX inhibition results in the restoration of the balance of $Ca^{2+}$ fluxes toward normal levels, with a greater fraction of $Ca^{2+}$ available for release from the cardiac SR.

This discovery identifies the $Na^+/Ca^{2+}$ exchange as a new target for heart failure therapy and offers a platform for the development of a new class of agents to improve cardiac muscle contractility. To date, there are no known specific $Na^+/Ca^{2+}$ exchange inhibitor compounds. The invention specifically pertains to the development of drugs or genetic therapeutic approaches which target $Na^+/Ca^{2+}$ exchange to improve $Ca^{2+}$ handling in muscle. The invention encompasses gene transfer methods for expressing exchanger inhibitory peptides (XIP) or XIP mimetic peptides or nucleic acid vectors which inhibit the expression of $Na^+/Ca^{2+}$ exchanger, as well as pharmacological compounds that have as their predominant effect inhibition of $Na^+/Ca^{2+}$ exchange.

DETAILED DESCRIPTION OF THE INVENTION

Introduction

Figure 1:
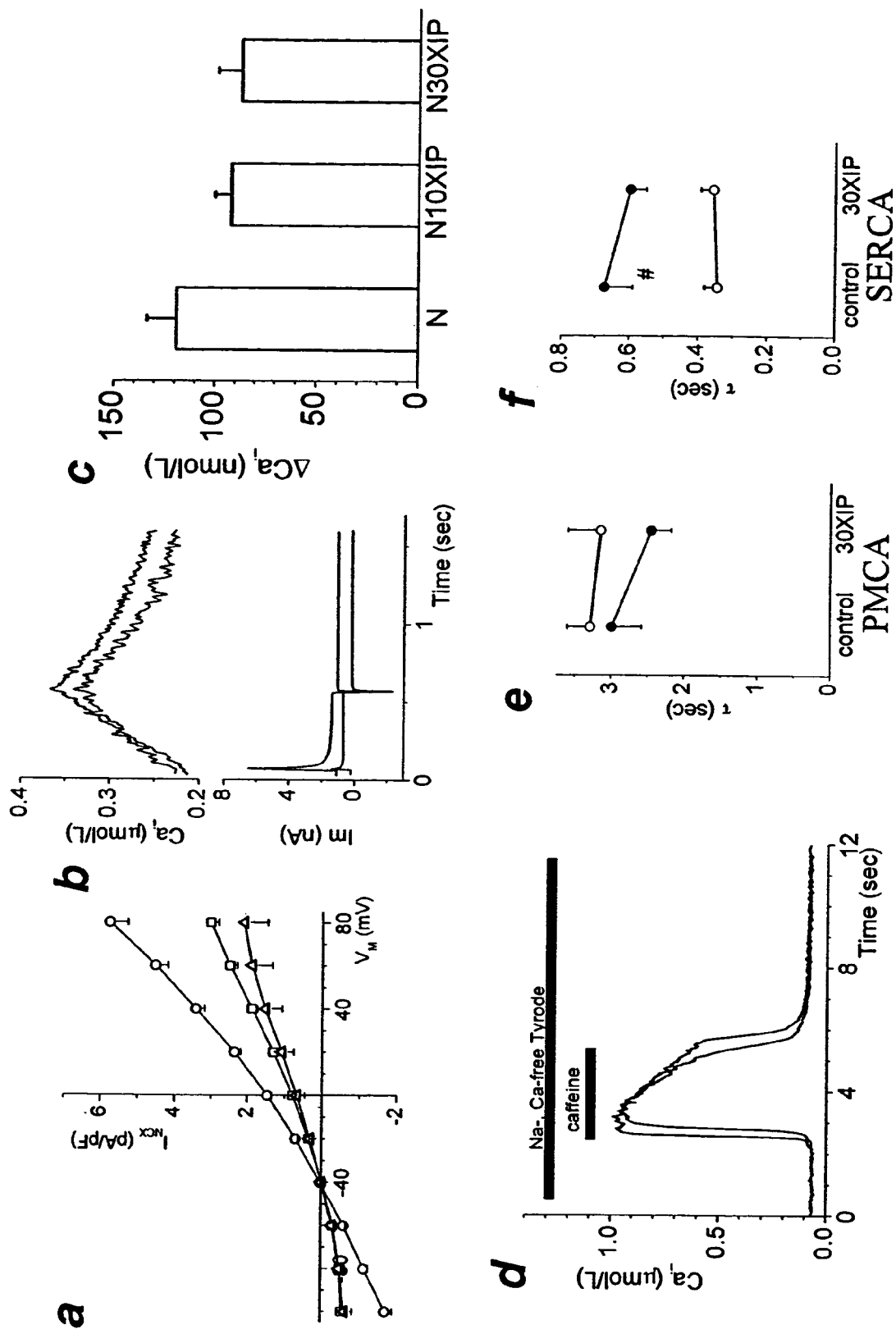
FIG. 1. Quantifying NCX block and selectivity.

Congestive heart failure is a disease of increasing incidence and mortality, which has an enormous economic impact worldwide. Nearly five million Americans are currently living with this condition, with 550,000 new cases diagnosed each year. Despite the magnitude of this problem, the treatment options are limited, and the disease has overall a remarkably bleak prognosis, with an average life expectancy of less than 5 years from diagnosis. The basis of this disease is constituted by the degradation of performance of the individual heart cells, with changes in multiple cellular mechanisms. Among them, an increase in calcium (Ca) extrusion from the cell by a membrane sodium/calcium ($Na^+/Ca^{2+}$) exchange protein contributes to the defective calcium handling, and leads to the decreased cardiac performance. This work describes for the first time how inhibiting the $Na^+/Ca^{2-}$ exchange restores the defective $Ca^{2+}$ signaling and provides a means of doing that as a potential treatment for heart failure. The proof of principle is achieved by partially inhibiting the $Na^+/Ca^{2+}$ exchange using a peptide (exchange inhibitory peptide, XIP), which restores $Ca^{2+}$ signaling in isolated heart cells from failing hearts. The invention originates the concept of Na/Ca exchange inhibition as a treatment for heart failure.

The present invention is a method of treating or preventing heart failure in a subject. The method includes enhancing cardiac contractility by inhibiting a sarcolemmal sodium/calcium exchanger.

In one embodiment the heart failure is a congestive heart failure. Congestive heart failures that are treated include those caused by a cardiomyopathy, including restrictive, dilative, and hypertrophic cardiomyopathies.

In another embodiment the heart failure is an acute heart failure including an acute heart failure that is a cardiogenic shock.

In one embodiment, the method includes administering to the subject an effective amount of a composition useful to inhibit the sarcolemmal sodium/calcium exchanger. Further embodiments include the composition wherein it comprises at least one peptide, and the embodiment wherein the peptide has the formula RRLLFYKYVYKRYRAGKQRG (SEQ. ID. NO 1).

Another embodiment is where the method comprises enhancing cardiac contractility by inhibiting the sarcolemmal sodium/calcium exchanger using a gene transfer. Further embodiments include the method wherein the gene is coding for a peptide useful to inhibit the sarcolemmal sodium/calcium exchanger. The method can have the gene coding for the peptide with the formula RRLLFYKYVYKRYRAGKQRG (SEQ. ID. NO 1).

Another embodiment includes that where the method comprises enhancing cardiac contractility by inhibiting the sarcolemmal sodium/calcium exchanger using RNA interference techniques.

Yet another embodiment includes that where the method comprises enhancing cardiac contractility by inhibiting the sarcolemmal sodium/calcium exchanger using anti-sense nucleotide techniques.

One embodiment of the invention is a pharmaceutical composition useful for treating or preventing heart failure. The composition includes at least one peptide useful to inhibit the sarcolemmal sodium/calcium exchanger in combination with a pharmaceutically acceptable carrier. The peptide can have the formula RRLLFYKYVYKRYRAGKQRG (SEQ. ID. NO 1).

*Canine tachycardia*-Induced Heart Failure Model

The *canine tachycardia*-induced model of heart failure was used for the experiments disclosing the invention, which faithfully reproduces the human disease while offering several advantages. The course of the disease is reproducible, time points prior to end-stage failure can be examined, and the confounding factors associated with studying human tissues (e.g., variations in the duration, etiology, or treatment) are absent. The decreased contractility and fractional shortening, and elevation of end diastolic pressure have been extensively documented in this model [Darniano, 1987 #20; Armstrong, 1986 #19]. Also present are chronic neurohumoral responses typical of heart failure, including the activation of the renin-angiotensin system [Armstrong, 1986 #19], increased norepinephrine levels [Armstrong, 1986 #19], decreased beta-adrenergic receptor density [Kiuchi, 1993 #5], and reduced adenylate cyclase activity [Ishikawa, 1994 #6]. Previous studies have documented the defects in cellular membrane and Ca handling mechanisms [O'Rourke, 1999 #46; Kaab, 1996 #76; Hobai, 2000 #37].

Induction of heart failure was carried out using protocols approved by the Institution's Animal Care and Use Committee. In brief, a VVI pacemaker (Medtronics) was implanted in mongrel dogs of either sex. Pacing at 240 bpm was maintained for 3–4 weeks, during which time the animals developed typical symptoms of heart failure including lethargy, loss of appetite, ascites, etc. Hemodynamic decompensation was confirmed by recording left ventricular (LV) pressure waveforms (under anesthesia with 25 mg/Kg tiopental) prior to sacrifice using a micromanometer—tipped LV catheter inserted through the right femoral artery. An increased end-diastolic pressure (EDP; N: 4.7±1.0 mmHg vs. F: 29.0±3.9 mmHg; p<0.001, n=10N and 7 F for this and following), slowed rate of pressure rise (dP/dt; N: 2738.1±170.9 mmHg/sec vs. F: 1216.6±89.5 mmHg/sec) and slowed relaxation rate (−dP/dt; N: −3591.7±238.4 mmHg/sec vs. F: −11260.1±85.3 mmHg/sec) were evident in F.

Methods

Isolation of Midmyocardial Cardiomyocytes

After left lateral thoracotomy, the heart was perfused with ice-cold cardioplegic solution, containing (mM): KCl 104; NaCl 32; $NaHCO_3$ 10, taurine 10, BDM (butanedione monoxime) 20, pH 7.4, and quickly excised. The region of the left ventricular free wall perfused by the left anterior descending coronary artery was excised, cannulated and perfused at 12 ml/min. The basic Ca-free isolation solution [Hobai, 1997 #15] contained, in mM: NaCl 130; KCl 4.5; $MgCl_2$ 5; HEPES 23; glucose 21; taurine 20; creatine 5; $NaH_2PO_4$ 1; Na pyruvate 5; pH 7.25 (titrated with NaOH), at 37° C., oxygenated with 100% $O_2$. The cardiac muscle was perfused in sequence with: 1) isolation solution with added 8 µM EGTA for 15 min.; 2) isolation solution with 50 µM Ca, 1 mg/ml collagenase (type I, 255 U/mg, Worthington Biochemical Corp., Freehold, N.J.) and 0.1 mg/ml protease (type XIV, Sigma Chemical Co., St. Louis, Mo.) for 12 min., and 3) isolation solution containing 100 µM Ca for 6 min. for washout. Chunks of well-digested ventricular tissue from the midmyocardial layer of the ventricle were dissected out (after removing the epicardial and endocardial layers) and cells were mechanically disaggregated, filtered through nylon mesh and stored in modified Tyrode's solution containing 1 mM Ca. The procedure yielded Ca-tolerant quiescent myocytes which survived well for up to 8 hours.

Single-Cell Electrophysiology Studies

Cells were placed in a heated chamber on the stage of an inverted fluorescence microscope (IX70, Olympus, Inc.) and superfused with a physiological salt solution. All experiments were carried out at 37° C. Borosilicate glass pipettes of 1–4 MΩ tip resistance were used for whole-cell recording with an Axopatch 1 D amplifier coupled to a Digidata I 200A personal computer interface (Axon Instruments, Foster City, Calif.) using custom-written software.

The external solution contained (mM): NaCl 140; KCl 4; $CaCl_2$ 2; $MgCl_2$ 1, HEPES 5; Glucose 10; niflumic acid 0.1 (to block $Ca^{2+}$-activated $Cl^-$ currents), pH 7.4. The pipette solution contained (in mM): K glutamate 125; KCl 19; $MgCl_2$ 0.5; MgATP 5; NaCl 10; HEPES 10; pH 7.25 and also 50 μM indo-I (pentasodium salt, Calbiochem, USA). The liquid junction potential between the pipette and bath was corrected.

$Ca_i$ Measurement $Ca_i$ measurement was performed as described previously [O'Rourke, 1999 #2461 using the K salt form of indo-1. Cellular autofluorescence was recorded before rupturing the cell-attached patch and subtracted prior to determining R (ratio of 405 mn emission/495 nm emission). $Ca_i$ was calculated according to the equation $Ca_i=K_d\beta\times[(R-R_{min})/(R_{max}-R)]$[Grynkiewicz, 1985 #73], using a $K_d$ of 844 nmol/L [Bassani, 1995 #87], and experimentally determined $R_{min}=1$, $R_{max}=4$ and $\beta=2$.

XIP Synthesis

XIP (RRLLFYKYVYKRYRAGKQRG) (SEQ ID NO. 1) was synthesized by the Biosynthesis and Sequencing Facility, Dept. of Biological Chemistry, Johns Hopkins University, kept as 20 mM stock in ethanol and added to the pipette solution (control experiments had equivalent amount of ethanol added, which had no effect on the parameters measured).

XIP Inhibits Selectively NCX

As there is currently no selective, externally applicable inhibitor of NCX (available compounds [Watano, 1996 #69] or inorganic blocking cations [Flobai, 1997 #51] are either non-selective, or preferentially block reverse-mode exchange [Watano, 1996 #69]), cellular responses were compared in the absence and presence of XIP (Li, 1991 #74), added directly to the intracellular solution. XIP has been shown to be an effective NCX blocker under various conditions (i.e., refs [Hobai, 1997 #51; Chin, 1993 #29; Li, 1991 #74]).

XIP in concentrations of 10 and 30 μM were used in the experiments, and an estimation of the actual degree of NCX inhibition obtained with these concentrations was needed. In a separate experiment[Hobai, 2000 #37] in normal (N) cells, NCX activity was measured as the $Ni^{2+}$-sensitive current elicited by depolarizations from −40 mV to various potentials in selective conditions and with $[Ca^{2+}]_i$ buffered to 200 nmol/L, as shown in FIG. 1a. In FIG. 1a, NCX current was measured selectively with $[Ca^{2+}]_i$ buffered to 200 mmol/L [Hobai, 2000 #37] (N, O). 10 (□) and 30 μM (Δ) XIP inhibited NCX by 45 and 55%, respectively (P<0.05 at all potentials except the reversal potential, n=22 cells from 6 animals (22/6), 6/2, 7/2 for control, 10 and 30 μM XIP), over the entire range of test potentials. The external solution was K-free (to block the inward rectifier $K^+$ current, and also the $Na^+/K^+$ pump) and also contained 100 μM niflumic acid (to block $Ca^{2+}$-activated $Cl^-$ currents), 10 μM strophanthidin ($Na^+/K^+$ pump inhibitor) and 10 μM nitrendipine (dihydropyridine antagonist). The pipette solution contained (mM): CsCl 110, NaCl 20, $MgCl_2$ 0.4, glucose 5, HEPES 5, $CaCl_2$ 1.75 and BAPTA 5. The mixture of BAPTA and Ca gave a free [Ca] of 200 nM (calculated using the "Maxchelator" program, D. Bers, Loyola University, Chicago). In these conditions, 10 and 30 μM XIP inhibited NCX by 45 and 55%, respectively (at +40 mV, FIG. 5a), and the block was mode-independent.

It was also important to estimate the degree of NCX inhibition in the minimally $Ca^{2+}$ buffered conditions that was used for the main ECC experiments as shown later in FIGS. 2–6. With the SR $Ca^{2+}$ uptake (and thus, indirectly, $Ca^{2+}$ release) blocked by thapsigargin, membrane depolarizations from −80 to +100 mV elicited reverse-mode NCX-mediated $[Ca^{2+}]_i$ increases [Hobai, 2000 #37] (FIG. 1b, c). Under these conditions, 10 and 30 μM XIP induced 23 and 27% NCX inhibition, respectively (FIG. 1b, c). At FIG. 1b, in N (and in the same experimental conditions as for FIGS. 2–6) with 1 μM thapsigargin, a depolarization from −80 mV to +100 mV induced reverse-mode NCX[Hobai, 2000 #37] (typical traces). FIG. 1c shows the NCX-induced $[Ca^{2+}]_i$ rise was inhibited to 77 and 73% of baseline levels by 10 and 30 μM XIP, respectively (n.s., n=8/5, 5/2 and 7/2 for N in control and with 10 and 30 μM XIP, respectively). Thus it was hypothesized that by raising average $[Ca^{2+}]_i$, NCX inhibition directly increases SR $Ca^{2+}$ uptake to simultaneously correct both SR $Ca^{2+}$ load and diastolic function.

XIP has been reported to inhibit both the sarcolemmal and SR $Ca^{2+}$ pumps in vitro [Enyedi, 1993 #59]. Therefore, it was important to establish that reversal of the failing phenotype was due to a selective effect on NCX. In the same experimental conditions as shown later in FIGS. 2–6, after a few pulses to load the SR, NCX was inhibited by a rapid application of a $Na^+$- and $Ca^{2+}$-free external solution, and caffeine was rapidly applied [Bassani, 1992 #66]. The time constants of $[Ca^{2+}]_i$ decay attributable to the sarcolemmal and SR $Ca^{2+}$ pumps were assessed during and after washout of caffeine, respectively [Bassani, 1992 #661. 30 μM XIP did not inhibit either transporter as shown in FIGS. 1d–1f). In FIGS. 1d.–f., a separate experiment was performed to confirm that XIP effect was not due to unspecific effects on other $Ca^{2+}$ handling mechanisms. With the NCX inhibited by a $Nat^+$-, $Ca^{2+}$-free external solution, SR release was induced with caffeine. During caffeine application, the only effective $Ca^{2+}$ extrusion mechanism is the plasmalemmal $Ca^{2+}$ pump (PMCA), whereas after caffeine removal, SR $Ca^{2+}$ pump starts also to remove cytosolic $Ca_i$ effectively [Bassani, 1992 #66]. The time constants of $Ca_i$ decay corresponding to PMCA and SERCA were not changed in the presence of 30 m XIP. d) Caffeine-evoked $Ca^{2+}$ transients, e–f) average data. (n=8/4 and 6/2 for N and 9/2 and 7/2 for F, in control and with 30 m XIP, respectively; P=n.s.). The disparity between the XIP sensitivity of the pumps shown earlier and the present findings is likely to be due to differences in the experimental conditions. For example, Enyedi, et al. [Enyedi, 1993 #59] measured PMCA and SERCA in membrane vesicles from rabbit erythrocyte and skeletal muscle preparations, respectively, and after proteolytic activation of PMCA.

Effect of XIP on Steady-State $[Ca^{2+}]_i$ Transients

Figure 2:
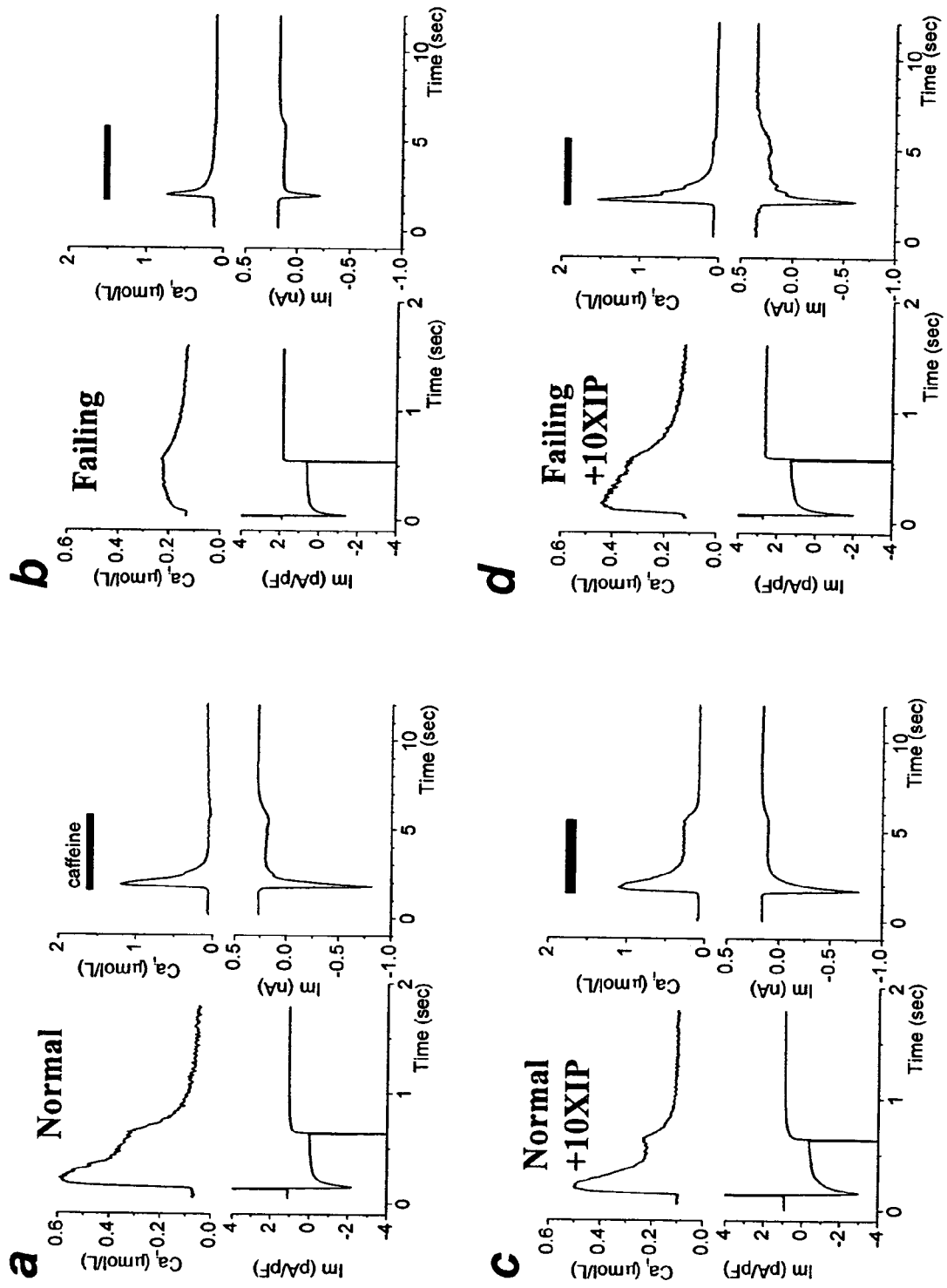
FIG. 2. XIP effects on $Ca^2$-induced $Ca^{2+}$ release.
Figure 3:
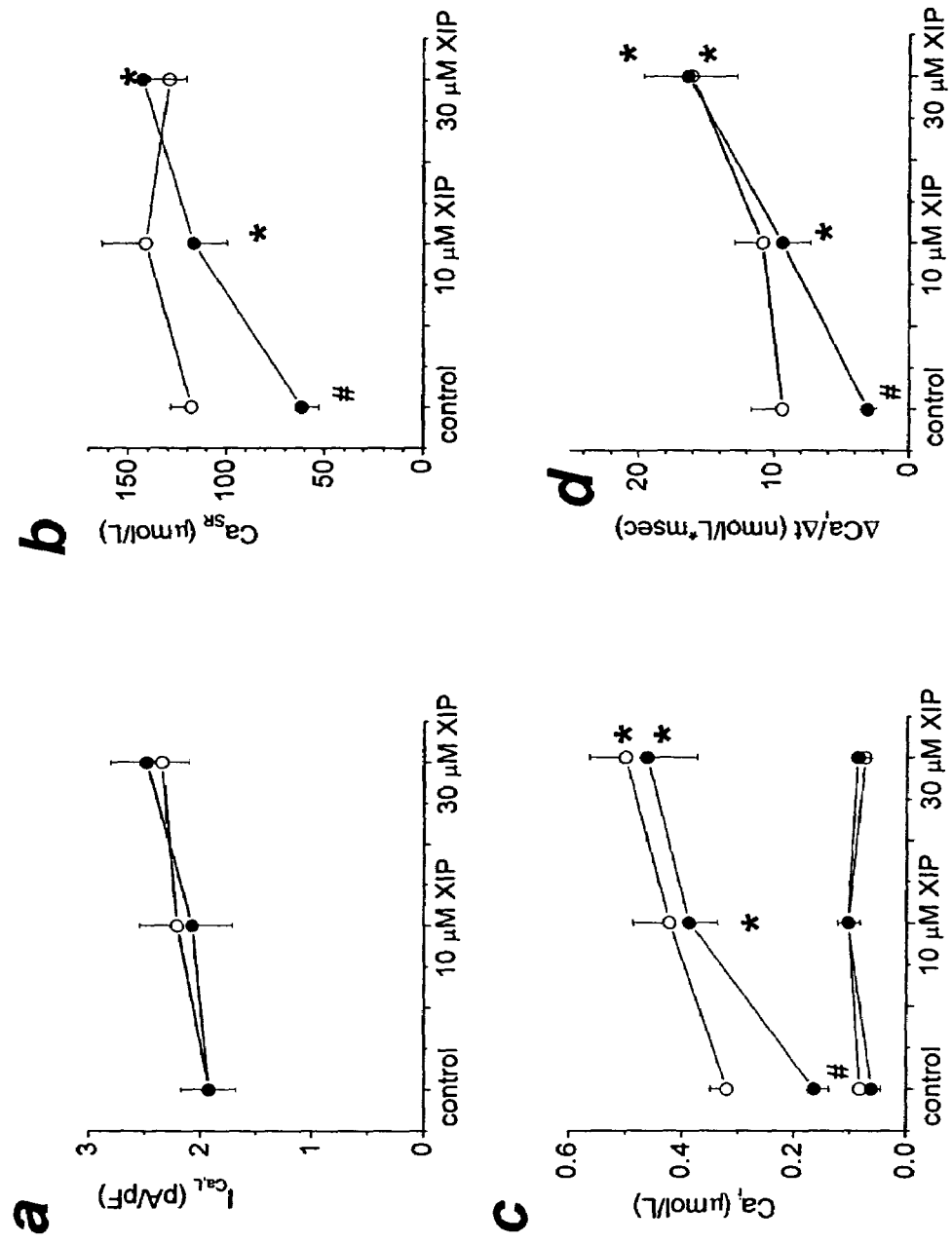
FIG. 3. XIP effects on $Ca^{2+}$-induced $Ca^{2+}$ release.

Cardiac cells isolated from normal (N) or failing (F) hearts were subjected to trains of depolarizations to assess the main mechanisms of $Ca^{2+}$-induced $Ca^{2+}$ release (CICR), i.e., trigger $Ca^{2+}$ entry through L-type $Ca^{2+}$ channels ($I_{Ca,L}$), the rate of rise (ΔCa/Δt) and amplitude (ΔCa) of the $[Ca^{2+}]_i$ transient, and the SR $Ca^{2+}$ load ($Ca_{SR}$, measured as the integral of NCX current during caffeine application [Hobai, 2000 #371; FIG. 2). The experimental protocol consisted of a train of 0.5 sec depolarizations from −80 mV to +10 mV, applied at 0.5 Hz until steady-state, followed by a rapid application of caffeine, to measure SR $Ca^{2+}$ load. Myocytes from failing hearts cells showed the characteristic $Ca^{2+}$ handling deficit, with depressed $[Ca^{2+}]_i$ transients and $Ca_{SR}$, and a normal $I_{Ca,L}$ (FIGS. 2–3). Internal equilibration with 10 μM XIP induced a large increase in the steady-state $Ca_{SR}$ and $[Ca^{2+}]_i$ transients, in the absence of any change in $I_{Ca,L}$. FIG. 2 shows the XIP effects on $Ca^2$-induced $Ca^{2+}$ release. Square voltage clamp pulses (−80 to +10 mV, 0.5 sec, at 0.5 Hz) were applied to isolated cardiac cells. After the $Ca_i$ transients reached steady-state, the train of depolarizations was stopped and caffeine was applied to measure $Ca_{SR}$ (FIGS. 2a–d). Steady-state membrane currents and $[Ca^{2+}]_i$ transients triggered by membrane depolarization (left) or caffeine (right), in myocytes from normal (N) or failing (F) hearts in the absence (FIG. 2a-b) or presence of 10 m XIP (FIG. 2c-d) in the intracellular solution. FIG. 3 also shows XIP effects on $Ca^{2+}$- induced $Ca^{2+}$ release. Average steady-state peak inward $I_{Ca,L}$ (FIG. 3a), $Ca_{SR}$ (as ⊠moles $Ca^{2+}$ stored in the SR per total cell volume, (FIG. 3b), diastolic and peak systolic $[Ca^{2+}]_i$ (FIG. 3c), and ΔCa/Δt (FIG. 3d) in N (○) and F (●), in the absence or presence of 10 or 30 μXIP. $I_{Ca,L}$ was similar in all six groups. At baseline, F cells had decreased $[Ca^{2+}]_i$ transients and reduced $Ca_{SR}$, which were normalized by XIP at 10 or 30 μM concentrations without affecting diastolic $[Ca^{2+}]_i$. In control conditions, n25/8 for N and 10/4 for F. For 10 μM XIP, n=14/3 and 10/5; and for 30 μM XIP n=15/4 and 12/2 for N and F, respectively. #P<0.05 between N and F groups for the same experimental condition.* P<0.05 within a group for XIP treatment versus baseline.

A smaller increase was also seen in normal myocytes. At a concentration of 30 μM, an additional ▪Ca increase was observed in both groups; in failing cells ΔCa was increased to 3.86-fold compared with the untreated group (FIG. 2c). Importantly, and somewhat unexpectedly, the enhancement of ECC occurred without a significant change in diastolic $[Ca^{2+}]_i$ (see later).

Effect of XI? on $[Ca^{2+}]_i$ Staircase

Figure 4:
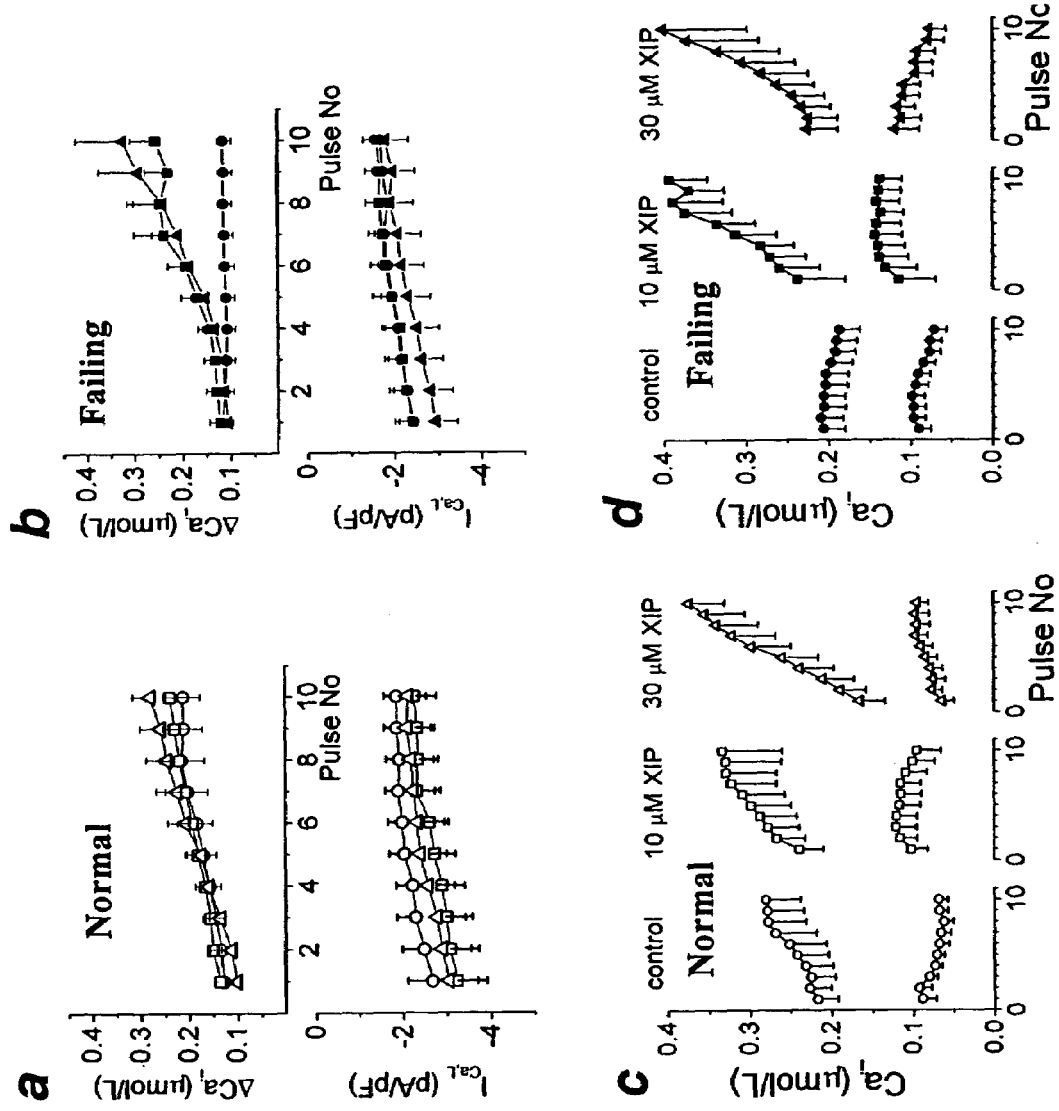
FIG. 4. XIP effect on the $Ca^{2+}$ staircase.

At FIG. 4 is shown the XIP effect on the $Ca^{2+}$ staircase. After a caffeine release, restarting the train of depolarizations induced gradually increasing cellular $Ca_i$ transients (i.e. staircase). FIG. 4a shows $[Ca^{2+}]_i$ transient amplitude and $I_{Ca,L}$ for the first 10 depolarizations (at 0.5 Hz) after a caffeine application. $[Ca^{2+}]_i$ transients increased gradually with pacing in N (○) and this effect was slightly accelerated by 10 (□) and 30 μM (Δ) XIP. Contrast FIG. 4b, where the positive $Ca^{2+}$ staircase was absent in F (●), but was restored by XIP (either 10, ■ or 30 μM, ▲). FIGS. 4c-d shows both diastolic and peak $[Ca^{2+}]_i$ are shown for the data presented in FIGS. 4a and b (n=12/5, 10/3, 9/3 and 11/4, 7/4, 7/2 for N and F, in control and with 10 and 30 μM XIP, respectively). The positive inotropic effect of XIP occurred without an associated increase in diastolic $[Ca^{2+}]_i$.

Immediately after a caffeine release (which unloaded the SR completely [Hobai, 2001 #48], and thus gave a similar starting point in all groups), repetitive square depolarizations induced in N a gradual increase in the $[Ca^{2+}]_i$ transients (positive staircase or "treppe"), following SR $Ca^{2+}$ loading. XIP slightly accelerated the pulse dependent $[Ca^{2+}]_i$ increase, as shown in FIG. 4 for the first 10 pulses, which lead, after 20–30 pulses, to the increased steady-state values shown in FIGS. 2–3. The positive staircase was characteristically absent in untreated F, but fully restored with the addition of 10 or 30 μM XIP (FIG. 4b). Again, the increase in the amplitude of the $[Ca^{2+}]_i$ transient was associated with a maintained or slightly decreased diastolic $[Ca^{2+}]_i$ (FIGS. 4c–d).

Effect of XIP on $[Ca^{2+}]_i$ Decay

Figure 5:
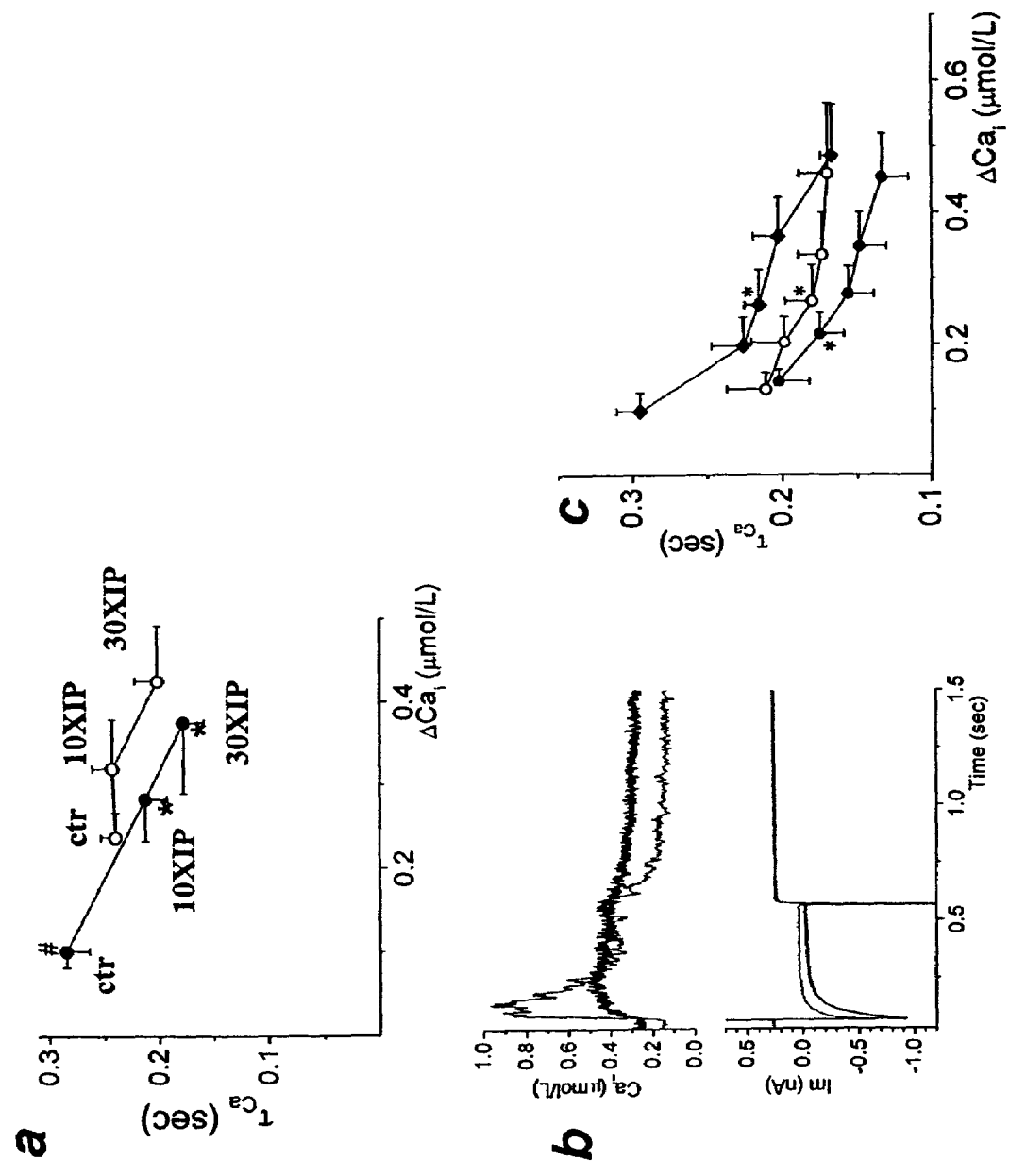
FIG. 5. XIP effects on $[Ca^{2+}]_i$ decay

At FIG. 5 is shown the XIP effects on $[Ca^{2+}]_i$ decay One potential adverse effect of NCX inhibition could have been a decrease in diastolic Ca decay and cell relaxation. However, for the steady-state $[Ca^{2+}]_i$ transients, XIP induced an unexpected acceleration of diastolic $[Ca^{2+}]_i$ removal kinetics ($\tau_{Ca}$) shown here at FIG. 5a in parallel with the increase in the amplitude of the $[Ca^{2+}]_i$ transient (○ N, ● F; n values as for FIG. 1). At FIG. 5b the relation between $\tau_{Ca}$ and ΔCa was reproduced in individual cells during the development of staircase (as in FIG. 3). Typical traces exemplifying the decreased $\tau_{Ca}$ associated with the increased $[Ca^{2+}]_i$ transient at steady-state (light gray trace) vs. first depolarization (black trace) after caffeine in a F cell with 30 μM XIP. At FIG. 5c. is shown average data for b. During the development of staircase, $Ca_i$ transients were selected equal to 150, 200, 250, and 300% of the first $Ca_i$ transient. $\tau_{Ca}$ of these $Ca_i$ transients were fitted and then plotted $\tau_{Ca}$ against ΔCa. In N (○, n=6/4;) the increase in ΔCa was associated with a significant decrease in $\tau_{Ca}$ (for this and other, * identifies the first data group whose $\tau_{Ca}$ was different from that of the first $Ca_i$ transient). A similar result was seen in F when staircase developed with either 10 or 30 μM XIP (, n=6/4). This relation was reproduced in F cells in which the gradual increase in the $[Ca^{2+}]_i$ transients was induced in the absence of XIP, by superfusion with 10 mM $Ca^{2+}$ Tyrode (♦, n=4/2). This it was hypothesized that, by raising average $[Ca^{2+}]_i$, NCX inhibition directly increases SR $Ca^{2+}$ uptake to simultaneously correct both SR $Ca^{2+}$ load and diastolic function.

Since NCX is a major $Ca^{2+}$ removal mechanism, especially in myocytes from failing hearts, it was anticipated that XIP may decrease the rate of diastolic $Ca^{2+}$ decay and adversely affect cell relaxation. However, the results indicated the contrary: at steady-state, the time constant of decay of the $[Ca^{2+}]_i$ transient upon repolarization to the holding potential ($\tau_{Ca}$; i.e., the combined NCX and SERCA actions) was decreased by XIP in both groups (FIG. 5a). This indicated that NCX inhibition was associated with an unexpected increase in the rate of SR $Ca^{2+}$ uptake (which was also consistent with the large increase in $Ca_{SR}$).

Upon closer inspection, $\tau_{Ca}$ acceleration proved to be dependent not directly on XIP, but secondary to the increase in $[Ca^{2+}]_i$ (FIG. 5b). In normal cells, during the development of the $Ca^{2+}$ staircase (as in FIG. 4), the increase in peak $[Ca^{2+}]_i$ was reproducibly associated with an acceleration of $\tau_{Ca}$ (FIG. 5c, open circles), as was previously described (i.e. ref [Schouten. 1990 #77]) and attributed to SERCA activation (i.e. sensitive to thapsigargin [Bassani. 1995 #64]). The same relation was found in failing cells, when the staircase was recovered in the presence of XIP (e.g. FIG. 5b for typical traces; FIG. 5c, solid circles). Finally, and clearly demonstrating that the acceleration of $Ca_i$ decay was not due to XIP in itself, but secondary to the ΔCa increase, FIG. 5c shows it could be reproduced in F cells in which the increase in the $[Ca^{2+}]_i$ transients was induced by an increase in external $Ca^{2+}$ concentration, in the absence of XIP (FIG. 5c, solid diamonds). $Ca^{2+}$-mediated SERCA activation was first described by Schouten in 1990 [Schouten, 1990 #77], and later coined "activity dependent acceleration of relaxation" [Bassani, 1995 #64]. Subsequent studies suggested it is probably an indirect mechanism, although the nature of the $[Ca^{2+}]_i$-sensitive mediator is still unclear. One possible mechanism suggested by some [Bassani, 1995 #64], but not all [Kassiri, 2000 #981] studies was calmodulin-dependent phosphorylation. Regardless of the mechanistic details, $[Ca^{2+}]_i$-mediated SERCA activation represents an effective autoregulatory mechanism that protects against cytosolic $[Ca^{2+}]_i$ overload. It is also a positive feedback mechanism, in which increased SR $Ca^{2+}$ release and uptake potentiate each other, a likely explanation for the large inotropic effect induced by a relatively modest (23–27%) degree of NCX block in both N and F.

Figure 6:
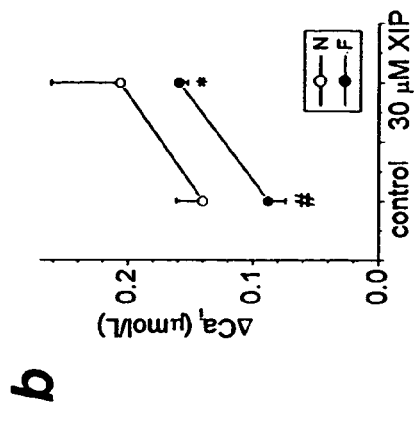
FIG. 6. The effect of XIP under current clamp conditions
Figure 6:
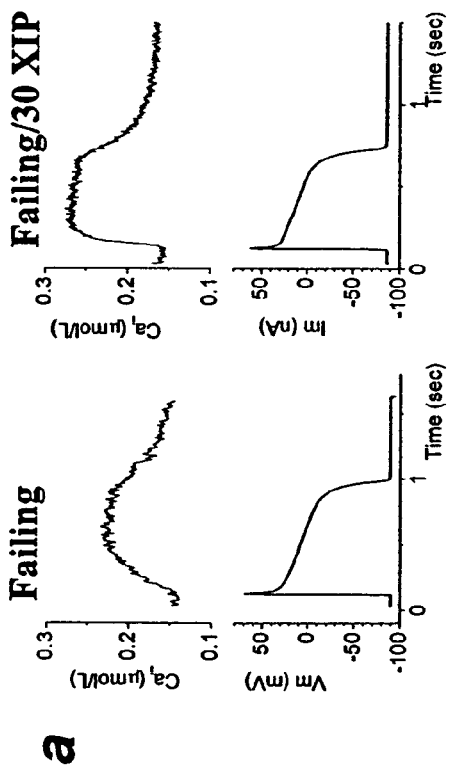
Figure 6:
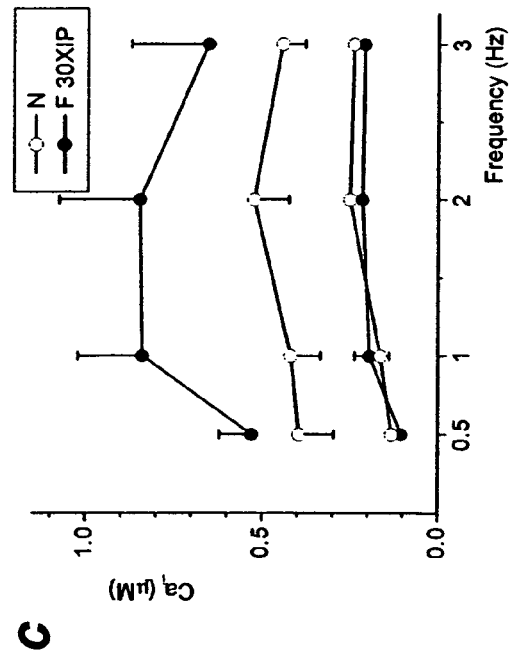

XIP Increases $Ca_i$ Transients During Action Potentials and at Different Frequencies FIG. 6 shows the effect of XIP under current clamp conditions At FIG. 6a is shown typical action potential-driven $Ca_i$ transients showing the effect of 30 μM XIP in F. At FIG. 6b, steady-state action potential driven $Ca_i$ transients (0.25 Hz) were significantly lower in F vs. N. 30 μM XIP significantly increased the $Ca_i$ transients in F and had a similar trend in N (n=9/3 and 5/2 for N and 8/4 and 4/2 for F, in control and with 30 μM XIP, respectively). At FIG. 6c, both the increase in ΔCa and maintenance of diastolic $Ca_i$ were reproduced at different stimulation frequencies (square pulses of 100 msec for 0.5–2 Hz and 50 msec for 3 Hz stimulation).

While the present experiments were designed to assess selectively CICR at the maximum $I_{Ca,L}$ amplitude, an action potential driven $Ca_i$ transient would likely include a component due to $Ca^{2+}$ entry through the NCX, which is likely to be relatively larger in F than in N [Dipla, 1999 #47]. Therefore it was of interest to determine if the positive inotropic effect of XIP was also evident in F cells during trains of action potentials in current clamp conditions. FIGS. 6a–b shows that action potential—triggered $Ca_i$ transients in F cells were significantly smaller than in N, and were normalized by 30 μM XIP. XIP had a similar, but less pronounced effect in N.

In addition, it was important to know whether the effects of XIP, and especially the maintenance of diastolic $Ca_i$ levels were still present when the cell was paced at higher frequencies, when the shortened diastole requires an increased rate of Ca extrusion. FIG. 6c demonstrates that this was indeed the case, and that failing cells in the presence of 30 μM XIP could be paced up to 3 Hz without development of diastolic Ca overload.

Summary and Conclusion

In summary, the present results demonstrate that partial inhibition of NCX is a powerful method for restoring ECC in heart failure. This effect is brought about by an improvement of SR $Ca^{2+}$ load and facilitation of the pulse-dependent positive $Ca^{2+}$ staircase due to a reduction in the amount of $Ca^{2+}$ "stolen" from the cell on each beat by NCX. Secondary $Ca^{2+}$-dependent stimulation of the SR $Ca^{2+}$ ATPase rate plays an additional important role in preventing diastolic $[Ca^{2+}]_i$ overload. This results represent the proof of therapeutic method for the development of NCX inhibitors as a new class of positive inotropic drugs in the treatment of congestive heart failure. Gene transfer technology making myocyte-targeted XIP expression a feasible therapy is also encompassed. While the NCX inhibitor was selective and mode-independent, the positive inotropic effect could be facilitated by a preponderantly forward-mode NCX inhibitor, and/or by block of PMCA (a lesser component of total $Ca^{2+}$ efflux).

The invention claimed is:

1. A method of treating or preventing heart failure in a subject, comprising:
enhancing cardiac contractility by inhibiting a sarcolemmal sodium/calcium exchanger; wherein the method comprises administering to the subject an effective amount of a composition useful to inhibit the sarcolemmal sodium/calcium exchanger, the composition comprising at least one peptide having the formula RRLL-FYKYVYKRYRAGKQRG (SEQ.ID.NO 1).

2. The method of claim 1 wherein the heart failure is a congestive heart failure.

3. The method of claim 1 wherein the heart failure is an acute heart failure.

4. The method of claim 3 wherein the acute heart failure is a cardiogenic shock.

5. The method of claim 2 wherein the congestive heart failure is caused by a cardiomyopathy.

6. The method of claim 5 wherein the cardiomyopathy is a dilative cardiomyopathy.

7. The method of claim 5 wherein the cardiomyopathy is a restrictive cardiomyopathy.

8. The method of claim 5 wherein the cardiomyopathy is a hypertrophic cardiomyopathy.

* * * * *